United States Patent [19]

Petzoldt et al.

[11] 4,353,985
[45] Oct. 12, 1982

[54] PROCESS FOR THE PREPARATION OF 11 β-HYDROXY STEROIDS

[75] Inventors: Karl Petzoldt; Klaus Annen; Henry Laurent; Rudolf Wiechert, all of Berlin, Fed. Rep. of Germany

[73] Assignee: Schering Aktiengesellschaft, Berlin, Fed. Rep. of Germany

[21] Appl. No.: 167,888

[22] Filed: Jul. 14, 1980

[51] Int. Cl.³ .............................................. C12P 33/08
[52] U.S. Cl. ........................................ 435/59; 435/911
[58] Field of Search ............................................ 435/59

[56] References Cited
U.S. PATENT DOCUMENTS 3,116,289 12/1963 Tanabe .................................... 435/59
3,152,154 10/1964 Ercoli ............................. 260/397.45
3,530,038 9/1970 Flines et al. ........................... 435/59

OTHER PUBLICATIONS
Chem. Abstracts 88:150628s, Kamano et al (1978).

*Primary Examiner*—Alvin E. Tannenholtz
*Attorney, Agent, or Firm*—Millen & White

[57] ABSTRACT

A process for preparing an 11β-hydroxy steroid of the formula

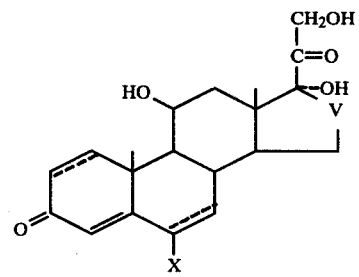

wherein
≡≡≡ represents a single bond or a double bond;
X is hydrogen, fluorine, chlorine or methyl; and
V is methylene, ethylene, ethylidene or vinylidene;

comprises fermenting an 11-deoxy steroid of the formula

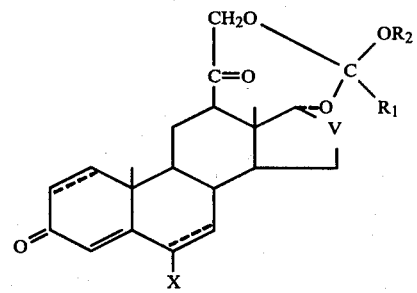

wherein
≡≡≡ , X and V are as defined above,
$R_1$ is hydrogen or $C_{1-6}$-alkyl; and
$R_2$ is $C_{1-6}$-alkyl;
with a fungal culture of a genus Curvularia.

7 Claims, No Drawings

PROCESS FOR THE PREPARATION OF 11 β-HYDROXY STEROIDS

BACKGROUND OF THE INVENTION

The present invention relates to an improved process for preparing 11β-hydroxy steroids.

As is known, 11β-hydroxy steroids having antiinflammatory activity (such as, for example, the corticoids: hydrocortisone, prednisolone, dexamethasone, betamethasone, prednylidene and flurandrenolone) are produced from naturally occurring steroids (such as diosgenin) by means of a very expensive, multistage partial synthesis.

Within the multistage synthesis of these compounds, the microbiological introduction of the 11β-hydroxy group into the steroid skeleton is normally the most expensive synthesis step and also the one wherein most of the losses are incurred due to the formation of by-products.

A process was developed in 1966 whereby the yield in the 11β-hydroxylation of 11-deoxy-17α-hydroxy steroids of the pregnane series was substantially increased by esterifying the 17α-hydroxy group, then hydroxylating using fungi of the genus Curvularia and saponifying the thus-obtained 11β-hydroxy-17α-acyloxy steroids (German Pat. No. 1,618,599). The 11-deoxy 17α-acyloxy steroids utilized as the starting compounds for this known process could be conventionally prepared, in turn, by chemical hydrolysis of 11-deoxy steroids of Formula II below. Disadvantageously, three-stage processes were necessarily required.

SUMMARY OF THE INVENTION

Accordingly, it is an object of this invention to provide a process for preparing 11β-hydroxy steroids via a process which is simple, inexpensive and achieves a high yield, inter alia.

Upon further study of the specification and appended claims, further objects and advantages of this invention will become apparent to those skilled in the art.

These objects have been achieved by this invention by preparing an 11β-hydroxy steroid of Formula 1

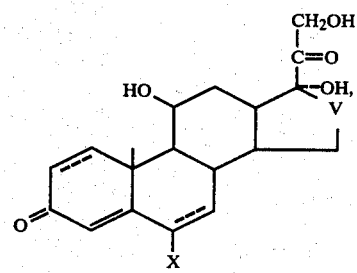

wherein

═ represents a single bond or a double bond;

X is hydrogen, fluorine, chlorine or methyl; and

V is a methylene, ethylene, ethylidene or vinylidene;

which comprises fermenting an 11-deoxy steroid of Formula II

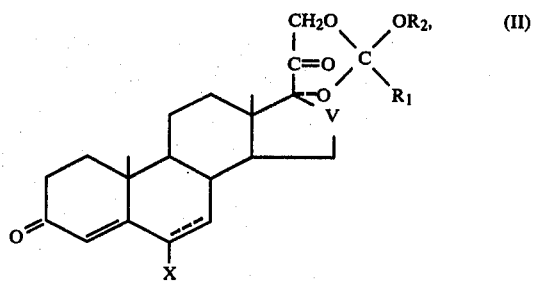

wherein

═, X, and V are as defined above, $R_1$ is hydrogen or alkyl of 1–6 carbon atoms; and $R_2$ is alkyl of 1–6 carbon atoms, with a fungal culture of the genus Curvularia.

DETAILED DISCUSSION

As compared to the previously known, three-stage procedure, the process of this invention has the advantage that it is less expensive, being a one-step process, and that higher yields of the product are obtained. The process of this invention, moreover, has the further surprising advantage that it can be conducted frequently with substantially higher substrate concentrations and with shorter reaction times than the conventional method. Also, the often rather difficult hydrolysis of the 11β-hydroxy-17α-acyloxy steroids, during which by-products are formed in most cases, is eliminated with the process of this invention. Thereby is also eliminated the expensive and loss-burdened purification of the thus-obtained products. This is necessary in most instances so that such products will satisfy the purity criteria required for active medicinal ingredients.

It is furthermore remarkable that it is possible by means of the process of this invention also to prepare very satisfactorily 11β-hydroxy-$\Delta^{1,4}$ steroids of Formula I from the corresponding 11-deoxy-$\Delta^{1,4}$ steroids of Formula II. According to the known state of the art, it is impossible to hydroxylate 11-deoxy-$\Delta^{1,4}$ steroids in good yields in the 11β-position.

Finally, it is also advantageous that it is unnecessary for conducting the process of this invention to employ, as starting compounds, pure forms of the 11-deoxy steroids of Formula II if these are prepared as crude products, for example, according to the following method.

Using a water trap, 300 ml of benzene is distilled off at a bath temperature of 110°–130° C. (glycerin bath) from a solution of 1 g (4 millimoles) of pyridinium tosylate and 10 g (28 millimoles) of the 17α,21-dihydroxy steroid in 80 ml of dimethylformamide and 700 ml of benzene, to remove traces of water. Thereafter, the mixture is briefly cooled, 24 ml (110–140 mmol) of orthocarboxylic acid trialkyl ester is added, and the residual benzene is distilled off within 1.5 hours. After the addition of 5.2 ml of pyridine, the reaction product is then further concentrated to dryness under a high vacuum.

The reaction proceeds quantitatively. The 17α-,21-(1-alkoxyalkylidenedioxy) steroid remaining after concentration is initially of an oily consistency, but in most cases is entirely crystallized after a short time. The degree of purity is wholly adequate for the subsequent microbiological hydroxylation; the residues of the reagents employed, which still adhere to the crystallized product, do not interfere with the enzyme catalysis. The D-homo steroids of Formula II are prepared analogously.

The pyridinium tosylate is produced as follows: 54 g of p-toluenesulfonic acid.H$_2$O is concentrated to dryness three times with a sufficient amount of benzene under vacuum, in order to remove the water. The residue is combined with 240 ml of pyridine; the mixture is stirred for ½ hour, and the product is precipitated with ether. The crystallized compound is vacuum filtered, washed with ether, and dried for 1 hour at 50° C. under vacuum.

The 11-deoxy steroids of Formula II can contain, as alkyl groups R$_1$ and R$_2$, branched or preferably straight-chain groups of 1–6 carbon atoms. Suitable alkyl groups R$_1$ and R$_2$ include, for example, methyl, ethyl, propyl, isopropyl, butyl, pentyl and hexyl. An especially preferred alkyl group R$_1$ is methyl. Particularly preferred alkyl groups R$_2$ are methyl and ethyl.

In the 11-deoxy steroids saturated in the 6,7-position of Formula II, the substituent X is preferably in the α-position.

It is surprising to one skilled in the art that the 11-deoxy steroids of Formula II can be hydroxylated and cleaved to the corresponding 11β-hydroxy steroids of Formula I. It was even less foreseeable that the desired products of the process are obtained by the method of this invention in very high yields (about 85–90% of theory).

Apart from the use of different starting compounds, and unless otherwise indicated herein, the process of this invention is conducted under conditions customarily employed for the 11β-hydroxylation of steroids with fungi of the genus Curvularia. See, for example, W. Charney and H. C. Herzog, Microbiol. Transformation of Steroids, 1967, Academic Press, New York, which disclosure is incorporated by reference herein.

Fungi of the genus Curvularia suitable for the hydroxylation include, for example, *Curvularia falcuta* QM-102 H, *Curvularia geniculata* IFO (6284), *Curvularia lunata* NRRL 2380, NRRL 2434, NRRL 2178, ATCC 12071 or IFO (6286), or *Curvularia maculans* IFO (6292).

In a suitable nutrient medium, submerged cultures are grown under aeration using the culturing conditions customarily employed for these microorganisms. Then the substrate (dissolved in a suitable solvent or preferably in emulsified form) is added to the cultures. The latter are fermented until maximum substrate conversion has been attained.

Suitable substrate solvents include, for example, methanol, ethanol, glycol monomethyl ether, dimethylformamide and dimethyl sulfoxide. The emulsification of the substrate can be effected, for example, by introducing this substrate via nozzles in micronized form or dissolved in a water-miscible solvent, (such as methanol, ethanol, acetone, glycol monomethyl ether, dimethylformamide or dimethyl sulfoxide), under strong turbulence, into (preferably demineralized) water containing the customary emulsifiers. Suitable emulsifiers include nonionic emulsifiers, e.g., ethylene oxide adducts or fatty acid esters of polyglycols. Examples of suitable emulsifiers include the commercially available surfactants "Tegin", "Tagat", "Tween", and "Span".

The emulsification of the substrates frequently affords an increased substrate throughput and accordingly a rise in the substrate concentration. However, in the process of this invention, it is, of course, also possible to utilize other methods for increasing the substrate throughput, as are well-known to a person skilled in the fermentation art.

The optimum substrate concentration, time of substrate addition, and duration of fermentation, are dependent on the structure of the substrate employed and on the type of microorganism used. These variables must be determined in each individual case by routine preliminary experiments familiar to those skilled in the art, as is generally required in microbiological steroid conversions.

The following 11β,17α,21-trihydroxy-4-pregnene-3,20-dione derivatives of Formula I can be prepared, for example, from the corresponding 11-deoxy steroids of Formula II according to the process of this invention:

11β,17α,21-trihydroxy-4-pregnene-3,20-dione,

11β,17α,21-trihydroxy-1,4-pregnadiene-3,20-dione,

11β,17α,21-trihydroxy-6α-methyl-4-pregnene-3,20-dione,

11β,17α,21-trihydroxy-6α-methyl-1,4-pregnadiene-3,20-dione,

11β,17α,21-trihydroxy-6-chloro-4,6-pregnadiene-3,20-dione,

11β,17α,21-trihydroxy-6-chloro-1,4,6-pregnatriene-3,20-dione,

11β,17α,21-trihydroxy-16α-methyl-4-pregnene-3,20-dione,

11β,17α,21-trihydroxy-16α-methyl-1,4-pregnadiene-3,20-dione,

11β,17α,21-trihydroxy-16β-methyl-4-pregnene-3,20-dione,

11β,17α,21-trihydroxy-16β-methyl-1,4-pregnadiene-3,20-dione,

11β,17α,21-trihydroxy-16-methyl-4-pregnene-3,20-dione,

11β,17α,21-trihydroxy-16-methylene-1,4-pregnadiene-3,20-dione,

11β,17α,21-trihydroxy-D-homo-4-pregnene-3,20-dione,

11β,17α,21-trihydroxy-D-homo-1,4-pregnadiene-3,20-dione,

6α-fluoro-11β,17α,21-trihydroxy-4-pregnene-3,20-dione,

6α-fluoro-11β,17α,21-trihydroxy-1,4-pregnadiene-3,20-dione.

The products of the process of this invention are well known pharmacologically active agents such as those mentioned previously.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for preparing an 11β-hydroxy steroid of the formula formula

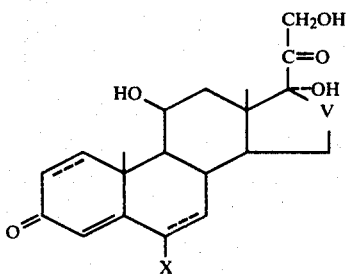

wherein

=== represents a single bond or a double bond;

X is hydrogen, fluorine, chlorine or methyl; and

V is methylene, ethylene, ethylidene or vinylidene;

which comprises fermenting an 11-deoxy steroid of the formula

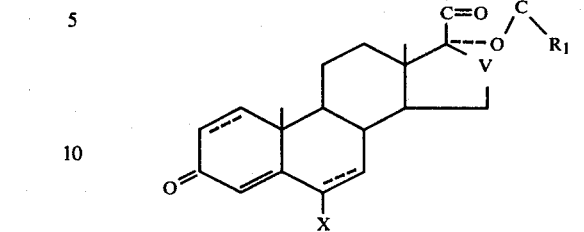

wherein
=== , X and V are as defined above;
$R_1$ is hydrogen or $C_{1-6}$-alkyl; and
$R_2$ is $C_{1-6}$-alkyl;
with a fungal culture of the genus Curvularia.

2. A process of claim 1, wherein the fungal culture is of the species *Curvularia lunata*.

3. A process of claim 1 or 2 wherein V is ethylene.

4. A process of claim 1 wherein both the starting 11-deoxy steroid and the product 11β-hydroxy steroid are $\Delta^{1,4}$ steroids.

5. A process of claim 1 wherein $R_1$ is methyl and $R_2$ is methyl or ethyl.

6. A process of claim 1 wherein the fungal culture is of the species *Curvularia falcuta* QU-102 H, *Curvularia genticulata* IFO (6284), *Curvularia lunata* NRRL 2380, NRRL 2434, NRRL 2178, ATCC 12071 or IFO (6286), or *Curvularia maculans* IFO (6292).

7. A process of claim 1 wherein the 11-deoxy steroid is added to the fermentation broth in emulsified form.

* * * * *